US 9,737,438 B2

(12) United States Patent
Rathjen

(10) Patent No.: US 9,737,438 B2
(45) Date of Patent: Aug. 22, 2017

(54) DEVICE FOR PROCESSING EYE TISSUE BY MEANS OF PULSED LASER BEAMS

(71) Applicant: Christian Rathjen, Bremen (DE)

(72) Inventor: Christian Rathjen, Bremen (DE)

(73) Assignee: ZIEMER OPHTHALMIC SYSTEMS AG (CH)

( * ) Notice: Subject to any disclaimer, the term of this patent is extended or adjusted under 35 U.S.C. 154(b) by 0 days.

(21) Appl. No.: 13/779,034

(22) Filed: Feb. 27, 2013

(65) Prior Publication Data
US 2013/0245617 A1   Sep. 19, 2013

Related U.S. Application Data

(60) Provisional application No. 61/610,677, filed on Mar. 14, 2012.

(51) Int. Cl.
*A61F 9/008* (2006.01)

(52) U.S. Cl.
CPC .......... *A61F 9/00802* (2013.01); *A61F 9/008* (2013.01); *A61F 2009/00872* (2013.01); *A61F 2009/00897* (2013.01)

(58) Field of Classification Search
CPC .. A61F 2009/00872; A61F 2009/00897; A61F 9/008; A61F 9/00802
USPC ........................................................ 606/4–6
See application file for complete search history.

(56) References Cited

U.S. PATENT DOCUMENTS 5,000,751 A * 3/1991 Schroder et al. .................. 606/4
2002/0173778 A1* 11/2002 Knopp ................... B23K 26/04
606/5

2004/0172106 A1*  9/2004  Imaizumi ........................ 607/89
2006/0224146 A1* 10/2006  Lin .................................... 606/4
2010/0262128 A1* 10/2010  Vogler .............................. 606/4
(Continued)

FOREIGN PATENT DOCUMENTS

DE     EP 2111831 B1 *  1/2010  ............. A61F 9/008
DE  WO 2010142311 A8 *  3/2011  ......... A61F 9/00827
(Continued)

*Primary Examiner* — Gary Jackson
*Assistant Examiner* — Boniface N Nganga
(74) *Attorney, Agent, or Firm* — Ostrolenk Faber LLP

(57) ABSTRACT

An ophthalmological device (1) for treating eye tissue by means of pulsed laser beams (L) comprises a laser system (12) which is designed, in a first mode of operation, to generate pulsed laser beams (L) with a wavelength in the NIR infrared range and, in a second mode of operation, to generate pulsed laser beams (L) with a wavelength in the UVA ultraviolet range. The ophthalmological device (1) moreover comprises a focusing system (10) with a projection optical unit (11), which is designed, in the first mode of operation, to project the pulsed laser beams (L) in the NIR infrared range into the lens (21) of the eye, which pulsed laser beams are focused to a first spot size (d1) by means of a first zoom function (101) for the purpose of disintegrating eye tissue, and, in the second mode of operation, to project the pulsed laser beams (L) in the UVA ultraviolet range into the cornea (22) of the eye, which pulsed laser beams are focused to a second spot size (d2) which is substantially smaller than the first spot size (d1) by means of a second zoom function (102), which differs from the first zoom function (101), for the purpose of creating tissue cuts.

17 Claims, 7 Drawing Sheets

(56) References Cited

U.S. PATENT DOCUMENTS

2011/0028948 A1     2/2011   Raksi et al. ........................ 606/4
2011/0172649 A1     7/2011   Schuele et al. .................... 606/4
2011/0178512 A1*   7/2011   Blumenkranz et al. ........... 606/6

FOREIGN PATENT DOCUMENTS

DE     WO 2013053367 A1 *   4/2013             A61F 9/008
EP      WO 2011/011202 A1     1/2011

* cited by examiner

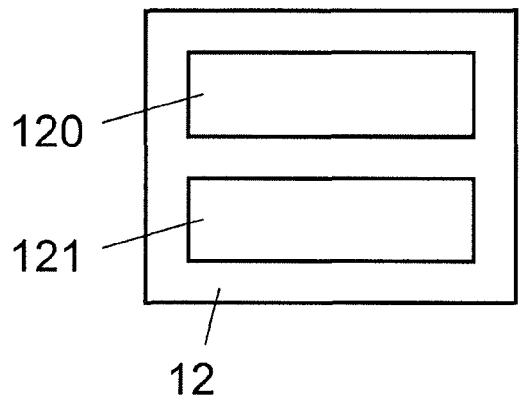
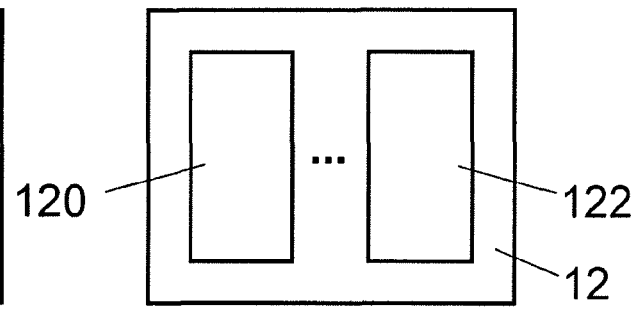
Fig. 2    Fig. 3
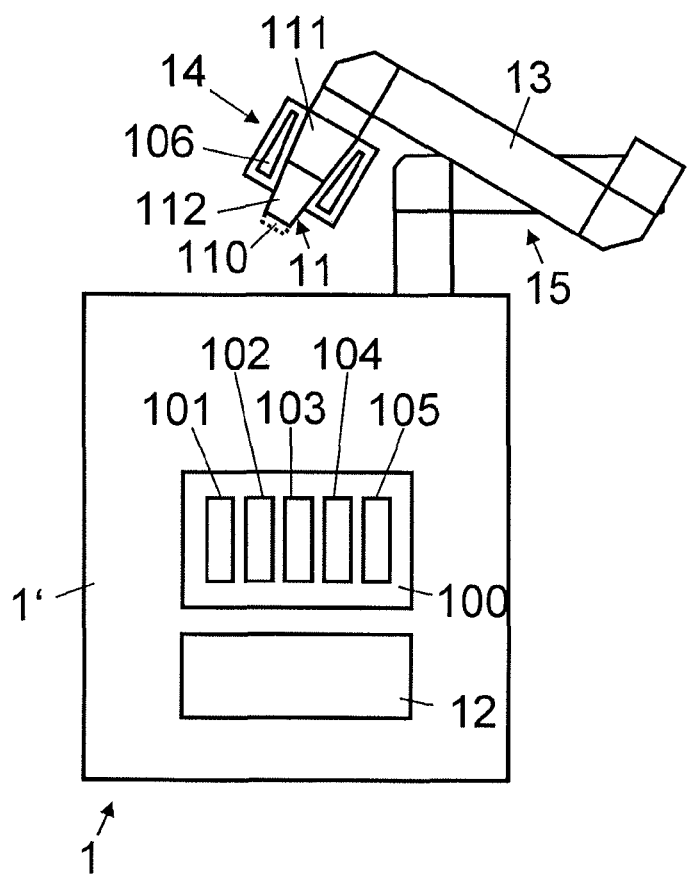
Fig. 4

DEVICE FOR PROCESSING EYE TISSUE BY MEANS OF PULSED LASER BEAMS

CROSS-REFERENCE TO RELATED APPLICATIONS

The present application claims benefit of and priority to U.S. Provisional Patent Application Ser. No. 61/610,677, entitled DEVICE FOR PROCESSING EYE TISSUE BY MEANS OF PULSED LASER BEAMS, filed Mar. 14, 2012, the entire content of which is hereby incorporated by reference herein.

BACKGROUND

Field of the Disclosure

Technical Field

The present invention relates to an ophthalmological device for treating eye tissue by means of pulsed laser beams. The present invention more particularly relates to an ophthalmological device for treating eye tissue by means of pulsed laser beams, which comprises a laser system which is designed, in a first mode of operation, to generate pulsed laser beams with a wavelength in the NIR infrared range and, in a second mode of operation, to generate pulsed laser beams with a wavelength in the UVA ultraviolet range.

Related Art

These days, vision defects such as myopia, hyperopia or astigmatism can be corrected permanently by means of a refractive-surgical treatment. Refractive-surgical treatments are surgical interventions on the eye which change the optical refractive power of the eye with the goal of approximating it to the best possible extent to a desired value. One of the most important methods in refractive surgery is the so-called laser-assisted in-situ keratomileusis (Lasik), in which the interior of the cornea is ablated by means of an excimer laser, after a corneal flap was previously partially severed and folded away. Such corneal flaps are cut using mechanical microkeratomes or by means of strongly focused femtosecond laser pulses. Suitable femtosecond laser systems generate laser pulses with pulse widths of typically 100 fs to 1000 fs (1 fs=$10^{-15}$ s).

The patent application WO 03/057100 describes a device for refractive laser surgery, which comprises a laser system for generating a pulsed laser beam with femtosecond laser pulses and a further laser system for generating a laser beam in the ultraviolet (UV) range. Both laser systems are preferably fed by a common pump laser source in the infrared range, with the UV laser beams being generated by frequency multiplication from the infrared light. In one embodiment variant, an excimer laser is used for generating the UV laser beam. The light beams from both laser systems are fed to a common scanner, which is used both for deflecting the femtosecond laser pulses when cutting the corneal flap and for deflecting the UV laser beam during the refractive correction of the cornea by surface ablation.

DESCRIPTION OF THE INVENTION

It is an object of the present invention to propose an improved ophthalmological device for treating eye tissue by means of pulsed laser beams, which comprises a laser system which is designed, in various modes of operation, to generate pulsed laser beams with different wavelengths, more particularly in the NIR infrared range in a first mode of operation and in the UVA ultraviolet range in a second mode of operation.

According to the present invention, these goals are achieved by the features of the independent claims. Further advantageous embodiments moreover emerge from the dependent claims and the description.

An ophthalmological device for treating eye tissue, more particularly for material processing in the eye tissue, by means of pulsed laser beams comprises a laser system which is designed, in a first mode of operation, to generate pulsed laser beams with a wavelength in the NIR infrared range and, in a second mode of operation, to generate pulsed laser beams with a wavelength in the UVA ultraviolet range.

The aforementioned goals are more particularly achieved by the present invention by virtue of the fact that the ophthalmological device comprises a focusing system with a projection optical unit, which is designed, in the first mode of operation, to project the pulsed laser beams in the NIR infrared range into the lens of the eye, which pulsed laser beams are focused to a first spot size by means of a first zoom function for the purpose of disintegrating eye tissue, and, in the second mode of operation, to project the pulsed laser beams in the UVA ultraviolet range into the cornea of the eye, which pulsed laser beams are focused to a second spot size which is substantially smaller than the first spot size by means of a second zoom function, which differs from the first zoom function, for the purpose of creating tissue cuts.

In particular, the focusing system is designed, in the first mode of operation and by using the first zoom function, to project the pulsed laser beams in the NIR infrared range onto an imaging surface situated in the lens of the eye and to focus said pulsed laser beams onto the first spot size and, in the second mode of operation and by using the second zoom function, to project the pulsed laser beams in the UVA ultraviolet range onto an imaging surface situated in the cornea of the eye and to focus said pulsed laser beams onto the second spot size.

In one embodiment variant, the focusing system comprises two optical systems, which can be set by the zoom functions to project the pulsed laser beams onto an imaging surface and to focus said laser beams to a spot size on the imaging surface. Hence the optical systems can be set by the zoom functions to project the pulsed laser beams onto an imaging surface determined by the relevant zoom function and to focus said pulsed laser beams on this imaging surface onto a spot size specified by the relevant zoom function.

In one embodiment variant, the focusing system comprises a drive system, which can be controlled by the zoom functions, for individual setting of the optical systems. The focusing system thus renders possible an automatic setting of the optical systems, controlled by the zoom functions, in such a way that the pulsed laser beams are projected onto an imaging surface determined by the relevant zoom function and are focused on this imaging surface to a spot size determined by the relevant zoom function.

In a further embodiment variant, the focusing system is designed, in the first mode of operation and by using the first zoom function, to set the optical systems to project the pulsed laser beams in the NIR infrared range onto the imaging surface situated in the lens of the eye and, on the imaging surface situated in the lens of the eye, to focus said pulsed laser beams onto the first spot size and, in the second mode of operation and by using the second zoom function, to set the optical systems to project the pulsed laser beams in the UVA ultraviolet range onto the imaging surface situated in the cornea of the eye and, on the imaging surface situated in the cornea of the eye, to focus said pulsed laser beams onto the second spot size.

In various embodiment variants, the focusing system comprises optical lenses that can be inserted into the beam path, deformable mirrors, mechanically embodied zoom curves for carrying out the zoom functions and/or zoom functions with digitized zoom curves for a control system.

In one embodiment variant, the laser system is designed, in the first mode of operation, to generate pulsed laser beams with a wavelength in the IR-A infrared range and, in a third mode of operation, to generate pulsed laser beams with a wavelength in the IR-B infrared range and the focusing system is designed, in the third mode of operation, to project the pulsed laser beams in the IR-B infrared range in focus into the sclera of the eye or the cloudy cornea for the purpose of disintegrating eye tissue.

In a further embodiment variant, the focusing system is designed, in the third mode of operation and by using a third zoom function, to project the pulsed laser beams in the IR-B infrared range onto an imaging surface situated in the sclera of the eye or in a cloudy cornea and to focus said pulsed laser beams onto a third spot size.

In a further aspect, the present invention relates to an ophthalmological device for treating eye tissue by means of pulsed laser beams, which comprises a laser system which is designed, in various modes of operation, to generate pulsed laser beams with different wavelengths and which comprises a focusing system with a projection optical unit, which is designed, in the various modes of operation, to project the pulsed laser beams with the different wavelengths into the eye tissue, respectively focused by means of a different zoom function associated with the relevant wavelength.

In one embodiment variant, the focusing system is designed, in various modes of operation, to project the pulsed laser beams in focus onto the imaging surface using a different intensity profile which is determined by a zoom function associated with the relevant mode of operation.

In one embodiment variant, the ophthalmological device comprises a control system which is designed to control the ophthalmological device in accordance with different modes of operation, wherein the modes of operation comprise at least one of the following:

a first mode of operation for disintegrating eye tissue of the lens of the eye by focusing pulsed laser beams in the IR-A infrared range by means of a first zoom function, a second mode of operation for creating horizontal tissue cuts in the cornea by focusing the pulsed laser beams in the UVA ultraviolet range by means of a second zoom function, a third mode of operation for disintegrating eye tissue of the sclera of the eye or the cloudy cornea by focusing pulsed laser beams in the IR-B infrared range by means of a third zoom function, a fourth mode of operation for creating tissue cuts in the capsular bag of the lens of the eye by focusing the pulsed laser beams in the UVA ultraviolet range by means of a fourth zoom function, and a fifth mode of operation for creating vertical tissue cuts in the cornea by focusing pulsed laser beams in the IR-A infrared range by means of a fifth zoom function.

The projection optical unit for the pulsed laser beams is preferably designed to be transparent in the UVA ultraviolet range and has a low numerical aperture NA, in particular a numerical aperture NA<0.5, for example a numerical aperture NA<0.3 or NA<0.2.

In one embodiment variant, the glasses used in the projection optical unit have a refractive index n<1.65. The glasses used in the projection optical unit are preferably made of fused quartz.

BRIEF DESCRIPTION OF THE DRAWINGS

In the following text, an embodiment of the present invention will be described on the basis of an example. The exemplary embodiment is illustrated by the following attached figures:

FIG. 2: shows a block diagram, which schematically illustrates a laser system comprising a laser source for generating a pulsed laser beam with an initial wavelength and a frequency convertor for generating a pulsed laser beam with a target wavelength from the laser beam with the initial wavelength.

FIG. 3: shows a block diagram which schematically illustrates a laser system comprising a plurality of laser sources which are respectively designed to generate pulsed laser beams with different wavelengths.

FIG. 4: shows a block diagram which schematically illustrates an ophthalmological device for treating eye tissue by means of pulsed laser beams, in which the laser system is arranged in a base station and in which the projection optical unit is arranged in an application head, which is attached to the base station by a support arm.

WAYS OF IMPLEMENTING THE INVENTION

Figure 1:
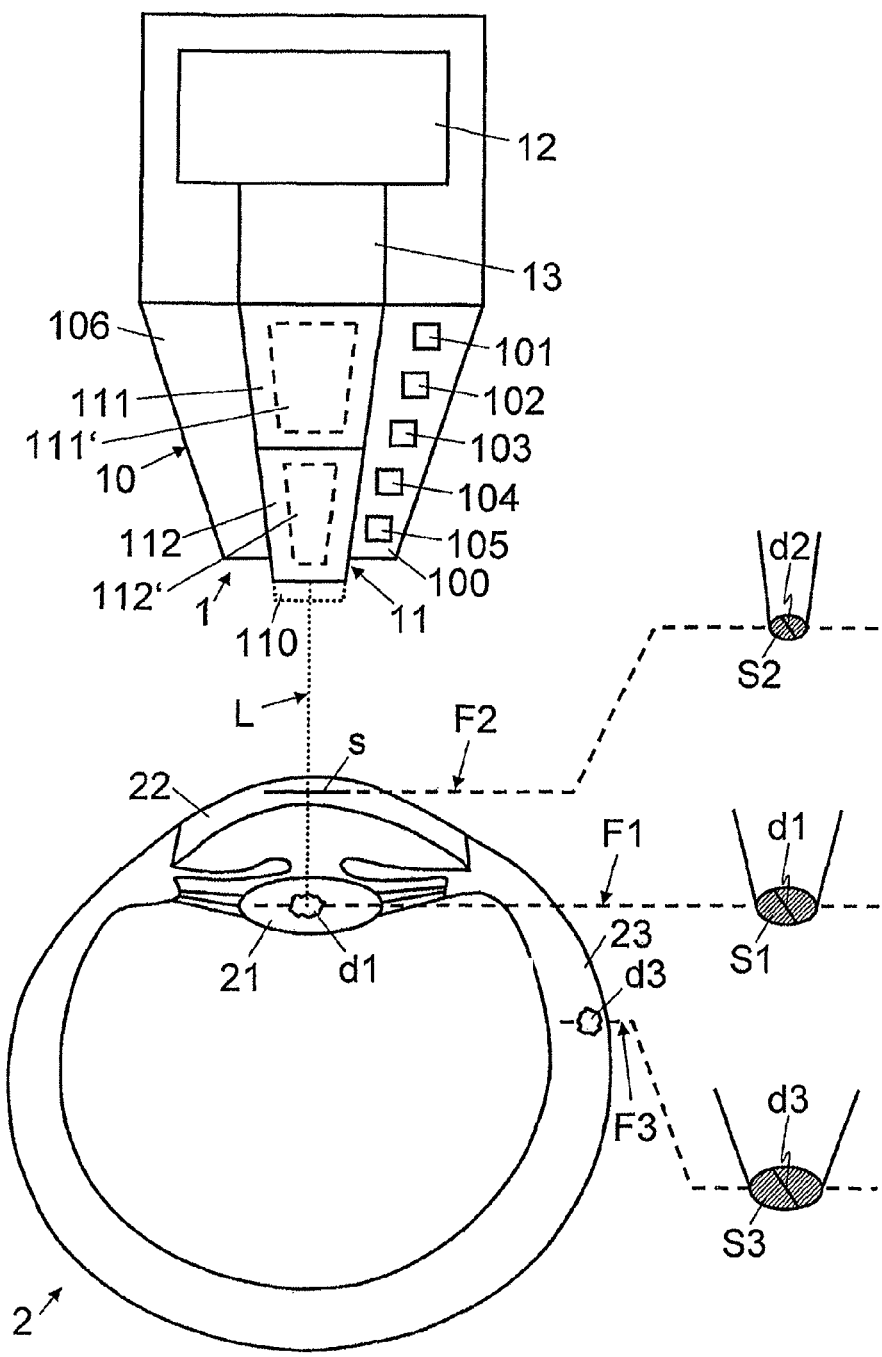
FIG. 1: shows a block diagram which schematically illustrates an ophthalmological device for treating eye tissue by means of pulsed laser beams, wherein different spot sizes are determined for the focused projection of the pulsed laser beams on imaging surfaces in the cornea, the lens of the eye and the sclera.

In FIGS. 1 and 4, reference sign 1 relates to an ophthalmological device for treating eye tissue, in particular for material processing in the eye tissue, by means of pulsed laser beams L. As illustrated schematically in FIGS. 1 and 4, the ophthalmological device 1 comprises a laser system 12, which is designed, in different modes of operation, to generate pulsed laser beams L, in particular femtosecond laser pulses (1 fs=$10^{-15}$ s), with different wavelengths. The ophthalmological device 1 moreover comprises a focusing system 10, which is designed, in the different modes of operation, to project the pulsed laser beams L with the different wavelengths into the eye tissue, onto different imaging surfaces with different spot sizes and/or intensity profiles, which pulsed laser beams are respectively focused by a different zoom function associated with the relevant wavelength, as will be described in more detail below.

In particular, the laser system 12 is designed to generate pulsed laser beams L in the NIR infrared range (near infrared range), e.g. selectable in the shorter wavelength IR-A infrared range, in particular in the region between 1000 nm and 1100 nm, or in the longer wavelength IR-B infrared range, in particular in the region between 1600 nm and 1700 nm, and in the UVA ultraviolet range (near ultraviolet range), in particular in the region between 300 nm and 400 nm.

In the embodiment variant shown in FIG. 2, the laser system 12 comprises a laser source 120, which is designed to generate pulsed laser beams L with an initial wavelength or initial frequency, and a frequency convertor 121, which is designed to generate pulsed laser beams L with the target frequency or target wavelength by frequency conversion from the pulsed laser beams L with the initial wavelength or initial frequency, for example laser beams in the UVA ultraviolet range by frequency multiplication from laser beams in the NIR infrared range or, vice versa, laser beams in the NIR infrared range by frequency division from laser beams in the UVA ultraviolet range.

In the embodiment variant shown in FIG. 3, the laser system 12 comprises a plurality of separate laser sources 120, 122, which are respectively designed to generate pulsed laser beams L in different wavelengths, for example a first laser source 120 in the IR-A infrared range, a second laser source in the IR-B infrared range and a third laser source 122 in the UVA ultraviolet range, and which can be activated selectively.

As illustrated schematically in FIGS. 1 and 4, the ophthalmological device 1 moreover comprises an optical transmission system 13 for transmitting the pulsed laser beam or the laser pulses from the laser system 12 to a projection optical unit 11, which is designed to project in focus the laser beam L or the laser pulses thereof into the eye tissue. As illustrated schematically in FIGS. 1 and 4, the projection optical unit 11 comprises two individually adjustable optical systems 111, 112, for example two lens groups with respectively one or more moveable lenses, and/or one or more deformable mirrors/lenses and insertable correction elements. The two optical systems 111, 112 are coupled to a drive system 106, which comprises one or more electric motors and is designed to set the optical systems 111, 112 individually, for example by displacing lenses in the projection direction (depth of focus) and/or normally to the projection direction (into/out of the beam path). The projection optical unit 11 is designed to be transparent to pulsed laser beams L in the UVA ultraviolet range. The glasses 111', 112' used in the projection optical unit 11 have a refractive index n<1.65. The glasses 111', 112' used in the projection optical unit 11 are made of fused quartz. The projection optical unit 11 has a low numerical aperture NA, more particularly a numerical aperture NA<0.5, for example a numerical aperture NA<0.3 or NA<0.2. The optical transmission system 13 moreover comprises a scanner system for lateral beam deflection in one or more scanning directions, which will not be discussed in any more detail.

As illustrated schematically in FIGS. 1 and 4, the ophthalmological device 1 moreover comprises a control system 100. The control system 100 comprises one or more processors or other programmed logic units, which are coupled to program and data storage devices, and/or electronic units for controlling the ophthalmological device 1. In particular, the control system 100 comprises a plurality of different zoom functions 101, 102, 103, 104, 105, which are designed to generate and transmit zoom control signals for controlling the drive system 106 or the optical systems 111, 112. As illustrated in FIG. 1, the control system 100 and the zoom functions 101, 102, 103, 104, 105 together with the optical systems 111, 112 of the projection optical unit 11 and the drive system 106 form a focusing system 10, which is controlled by the zoom functions 101, 102, 103, 104, 105, as will be described in more detail below.

In the embodiment variant shown in FIG. 4, the ophthalmological device 1 comprises a base station 1', in which the laser system 12 and the control system 100 are arranged. In the embodiment variant of FIG. 4, the projection optical unit 11 and the drive system 106 are arranged in an application head 14, which can be placed onto the eye 2 manually and for example touches the eye 2 by means of a transparent contact body 110, which is fixedly or removably coupled to the application head 14. The application head 14 is attached to the base station 1' by means of a support arm 15 and comprises the optical transmission system 13, which optically connects the laser system 12 to the projection optical unit 11. The support arm is embodied as, for example, an inherently rigid support arm or as a moveable support arm, for example a moveable support arm as per EP 1 731 120.

The various selectable zoom functions 101, 102, 103, 104, 105 of the control system 100 are respectively designed to control the focusing system 10 in such a way that the pulsed laser beam L (or the laser pulses thereof) is projected onto an imaging surface F, F1, F2, F3, specifically defined for the relevant zoom function 101, 102, 103, 104, 105, as a result of which the treatment depth is determined, and that the pulsed laser beam L (or the laser pulses thereof) is focused on this imaging surface F with a spot size d specifically defined for the relevant zoom function 101, 102, 103, 104, 105 and a defined intensity profile in the cross section of the laser beam L. The zoom functions 101, 102, 103, 104, 105 are designed to actuate the drive system 106 for parallel (simultaneous) or sequential (successive) setting of the optical systems 111, 112 by transmitting the corresponding zoom control signals to the drive system 106 of the focusing system 10. A person skilled in the art will understand that, in an alternative embodiment variant, the zoom functions 101, 102, 103, 104, 105 can be embodied as mechanical zoom curves. The zoom functions 101, 102, 103, 104, 105 therefore render it possible to project the pulsed laser beam L or the laser pulses thereof onto the imaging surface F, F1, F2, F3 at the desired treatment depth and to (re)focus the spot to have the desired spot size d, d1, d2, d3 with the desired intensity profile on this imaging surface F, F1, F2, F3.

Figure 5:
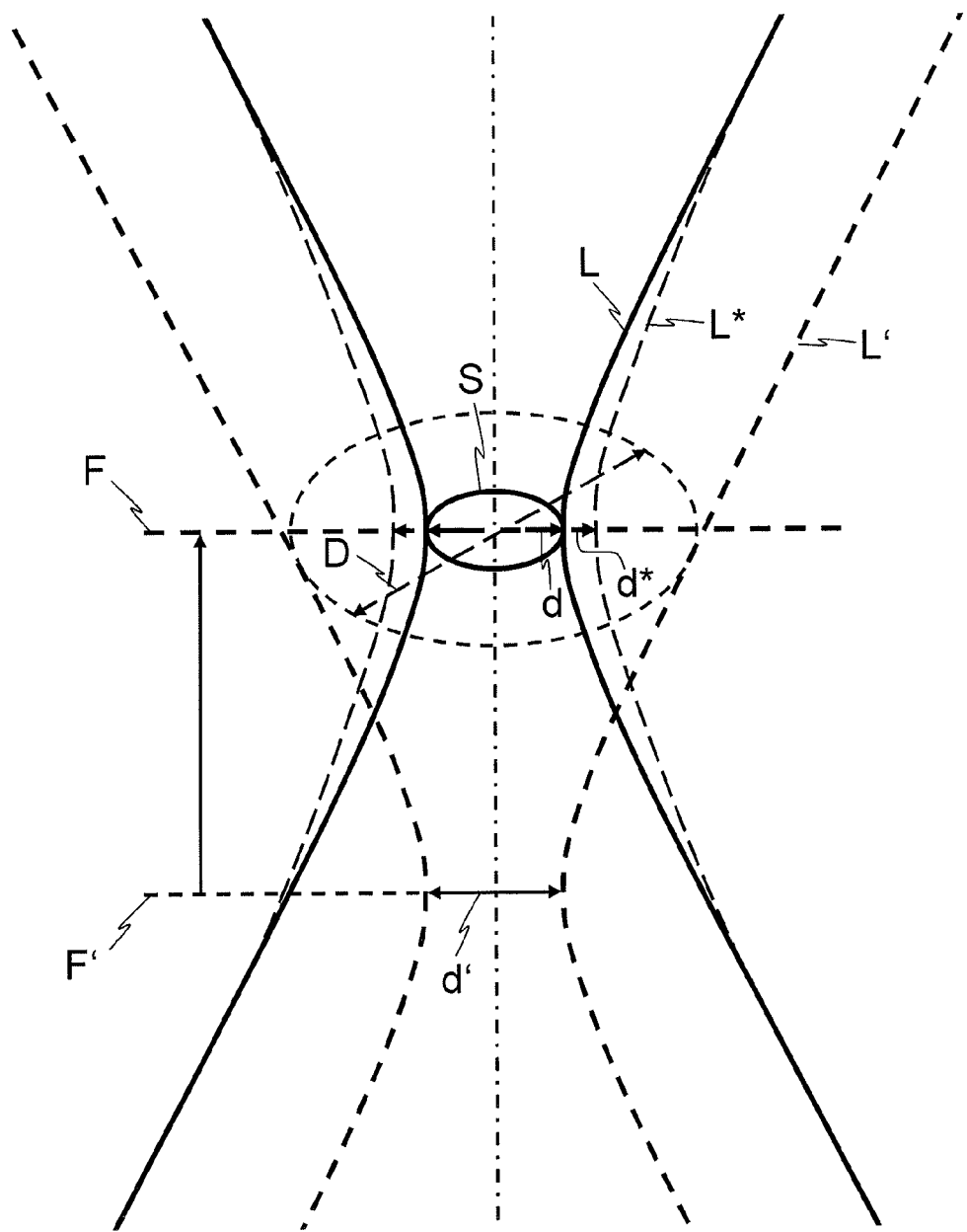
FIG. 5: shows a schematic illustration of profiles of a pulsed laser beam in different states, in which the pulsed laser beam is projected onto various imaging surfaces and respectively focused with a different defined spot size.

In FIG. 5, reference signs L', L*, L refer to pulsed laser beams which, with the laser beam profiles thereof, e.g. Gaussian laser beam profiles, are illustrated in different states of the focusing system 10, with the center axis of the laser beam L', L*, L or the projection direction being denoted by the reference sign z.

Reference sign L' refers to the pulsed laser beam in a first state, in which the narrowest beam waist of the beam profile is projected onto the imaging surface F' with a spot size having a diameter d'. Thus, in this first state, the pulsed laser beam L' is projected onto the projection or imaging surface F'. In this first state, the beam profile on the upper imaging surface F has a diameter D, which is significantly greater than the diameter d' thereof on the imaging surface F'.

Reference sign L* refers to the pulsed laser beam in the state in which the focus of the pulsed laser beam was shifted from the imaging surface F' to the imaging surface F. In this second state, as can be identified in FIG. 5, the pulsed laser beam L* is projected with a wider beam waist d*>d' onto the projection or imaging surface F.

Reference sign L refers to the pulsed laser beam in a third state, in which the narrowest cross section of the beam profile (spot S) with a spot size having a diameter d=d' is projected onto the imaging surface F, wherein this diameter d is smaller than the diameter d* in the second state. Thus, in the third state, the pulsed laser beam L is projected onto the imaging surface F as a spot S with a spot size having a diameter d=d', refocused from the spot size with diameter d* to the spot size with diameter d=d'.

The zoom functions 101, 102, 103, 104, 105 or zoom control signals control the drive system 106 or the optical systems 111, 112 in such a way that the focusing system 10, proceeding from an initial state, e.g. the above-described first or second state, is guided into a target state, e.g. the above-described third state, in order to project the pulsed laser beam L or the laser pulses thereof onto the imaging surface F, F1, F2, F3, which is defined by the relevant zoom function 101, 102, 103, 104, 105 and is situated at the defined treatment depth, and to focus said pulsed laser beam or said laser pulses thereof on this imaging surface F, F1, F2, F3 with a spot size d, d1, d2, d3 determined by the relevant zoom function and with a (radial) intensity profile determined by the relevant zoom function.

Figure 6:
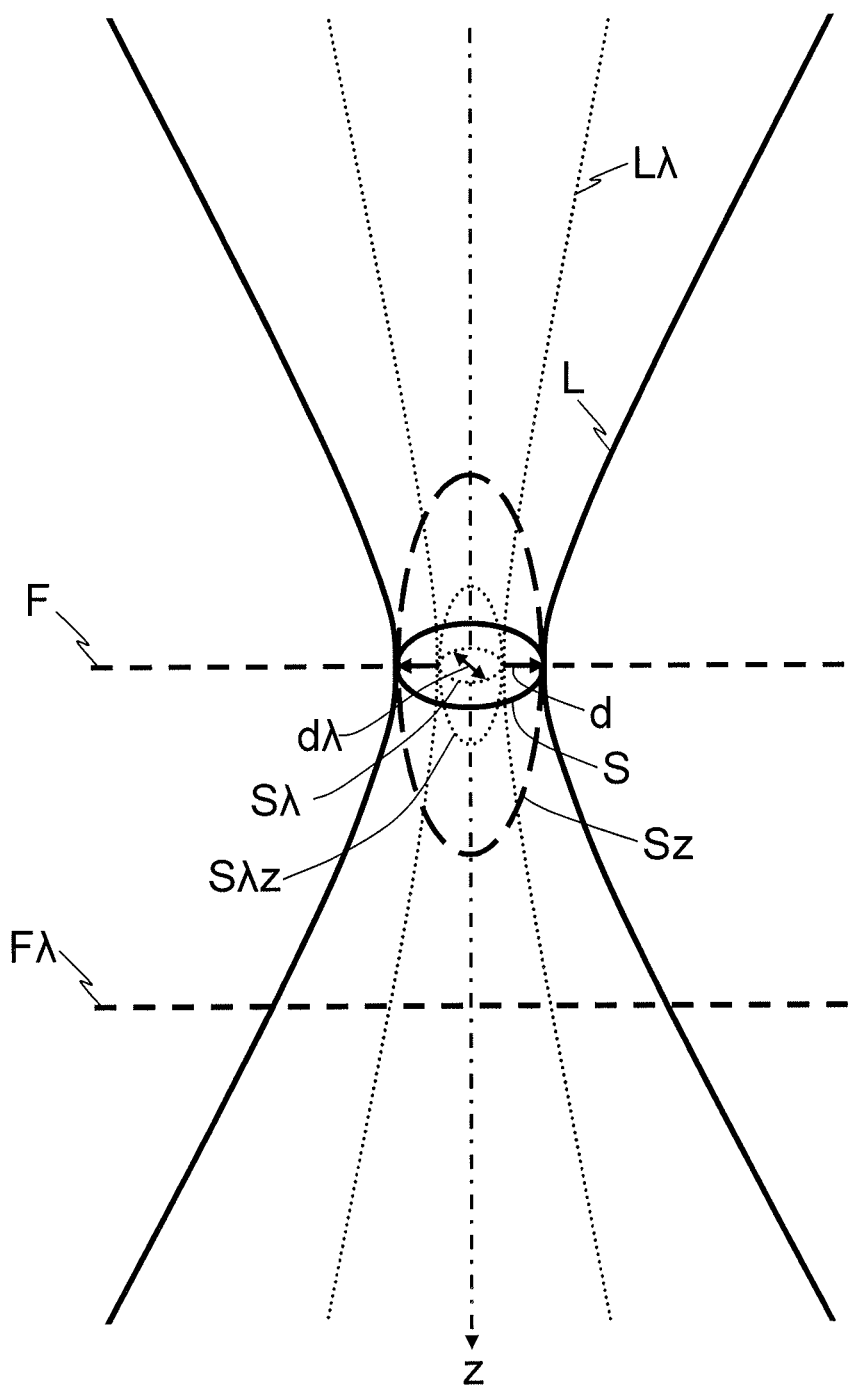
FIG. 6: shows a schematic illustration of profiles of pulsed laser beams with different wavelengths, which are projected onto an imaging surface and focused with a different spot size.

FIG. 6 schematically illustrates the laser beam profiles of pulsed laser beams L, L$\lambda$ with different wavelengths in the case of (re)focused projection onto the imaging surface F, wherein the pulsed laser beam L has a longer wavelength, e.g. is in the NIR infrared range (near infrared range), than the pulsed laser beam L$\lambda$, e.g. which is in the UVA ultraviolet range (near ultraviolet range). If the wavelength is modified, the focus is displaced in the projection direction z, i.e. if the settings of the projection optical unit remain unchanged, the imaging surfaces F, F$\lambda$ are different in the case of laser beams L, L$\lambda$ with different wavelengths, as illustrated schematically in FIG. 6. Since, in addition to the displacement of the focus or the imaging surfaces F, F$\lambda$, the focusing is not optimal either, different zoom functions are provided for different wavelengths. As can be seen in FIG. 6, the selection of a shorter wavelength laser beam L$\lambda$ reduces the spot size compared to the spot size of a longer wavelength laser beam L, i.e. the diameter d$\lambda$ of the spot S$\lambda$ of the shorter wavelength laser beam L$\lambda$ is smaller than the diameter d of the spot S of the longer wavelength laser beam L, d$\lambda$<d. A smaller spot size renders possible finer and more precise tissue cuts with less gas formation and reduced impairment of (damage to) surrounding tissue. In FIG. 6, reference signs Sz and S$\lambda$z denote the schematically illustrated extent of the spots S, S$\lambda$ along the projection direction z, wherein the extent (i.e. the length) of this spot extent Sz, S$\lambda$z in the projection direction z does not only depend on the wavelength of the laser beam L, L$\lambda$ but also on the numerical aperture NA of the projection optical unit 11: Sz, S$\lambda$ z$\propto\lambda/NA^2$. The spot extent Sz, S$\lambda$z in the projection direction z is used for creating tissue cuts in the projection direction z (vertical cuts) in selected modes of operation in order to cut more efficiently, i.e. quicker, with fewer pulses, for example in the first mode of operation described below for creating vertical tissue cuts in the lens 21 of the eye in order to segment the latter or in the fifth mode of operation described below for creating vertical tissue cuts in the cornea 22 in order to cut the latter in lamellar or penetrating fashion for a partial or complete corneal transplant.

The control system 100 selects the wavelength of the pulsed laser beam L and the zoom function 101, 102, 103, 104, 105 to be carried out, with associated imaging surface F, F1, F2 (treatment depth), spot size d and intensity profile, which are respectively dependent on a selected mode of operation. By way of example, the modes of operation described below can be selected and carried out depending on the embodiment variant and configuration. By way of example, the current mode of operation is selected and activated by the user via a user interface, or it is selected and activated automatically by means of the control system 100 depending on a detected device type of the application head 14, of the projection optical unit 11 and/or of the contact body 110, which are at this time connected to the ophthalmological device 1. By way of example, the device type is a mechanical, electrical, electronic, optical and/or electromagnetic identification, which is attached to the application head 14, to the projection optical unit 11 and/or in/to the contact body 110 and detected by a corresponding detector of the ophthalmological device 1 and transmitted to the control system 100.

Figures 7, 8:
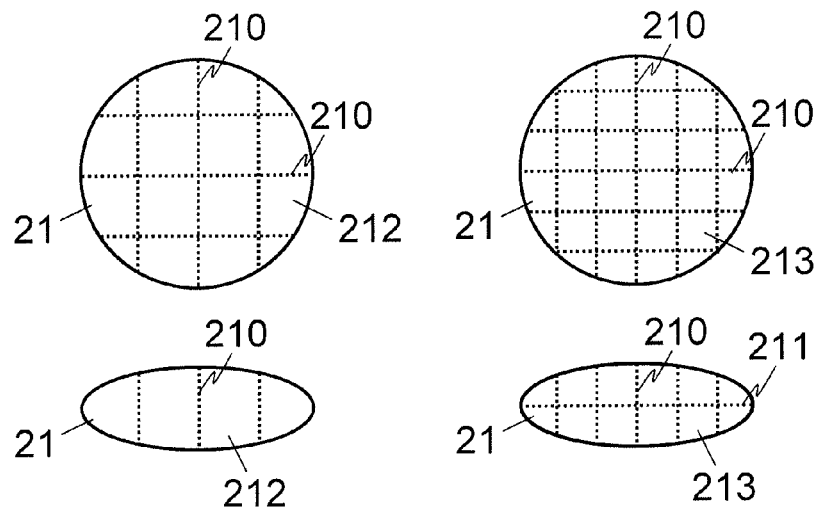
FIG. 7: schematically shows a plan view (top) and cross section (bottom) of a fragmentation of the lens of the eye with vertical tissue cuts, which extend parallel to the projection direction of the pulsed laser beam.
FIG. 8: schematically shows a plan view (top) and cross section (bottom) of a fragmentation of the lens of the eye with vertical and horizontal tissue cuts, which extend parallel or normal to the projection direction of the pulsed laser beam.

A first mode of operation is provided for disintegrating eye tissue in the lens 21 of the eye by focusing, by means of a first zoom function 101, pulsed laser beams L in the IR-A infrared range onto the imaging surface F1 with a spot S1, which has a spot size with a diameter d1 (see FIG. 1). As respectively illustrated schematically in the plan view (top) and cross section (bottom) in FIGS. 7 and 8, the first mode of operation is used, for example, for fragmenting the lens 21. In the example in FIG. 7, the lens 21 is divided into segments 212 by vertical cuts 210 extending in the projection direction z, in the simplest case by means of two vertical cuts 210 which cross in the center of the lens 21. In the example shown in FIG. 8, there moreover is also at least one horizontal cut 211, extending normally with respect to the projection direction z, in order to break the lens 21 down into smaller volume elements ("slice and dice"). The disintegration of eye tissue is of particular interest in the case of cataract operations for removing the lens core. Large beam waists in combination with large pulse energies are particularly efficient in the fast disintegration of lens tissue. As a result of the low intraocular absorption, IR-A is the preferred wavelength for applications in the lens 21.

A second mode of operation is provided for creating horizontal (i.e. extending substantially parallel to a reference surface applied on the cornea 22, e.g. by means of a contact body 110) tissue cuts s in the cornea 22 by focusing, by means of a second zoom function 102, the pulsed laser beams L in the UVA ultraviolet range onto the imaging surface F2 with a spot S2, which has a spot size with a diameter d2 (see FIG. 1). It is possible to create small beam waists by using UVA and adapted zoom functions. Small beam waists in combination with small (sufficient in the case of small beam waists) pulse energies enable cuts with optical surface quality and precise cut geometries. In contrast thereto, the use of IRA with large beam waists, which are ideal for applications in the lens 21, would lead to optically rough surfaces due to the large beam waists and to strong gas development due to the high pulse energies, with subsequent deformation of the cut surfaces. This is undesirable for applications in the region of the optical zone of the cornea 22.

Figure 9:
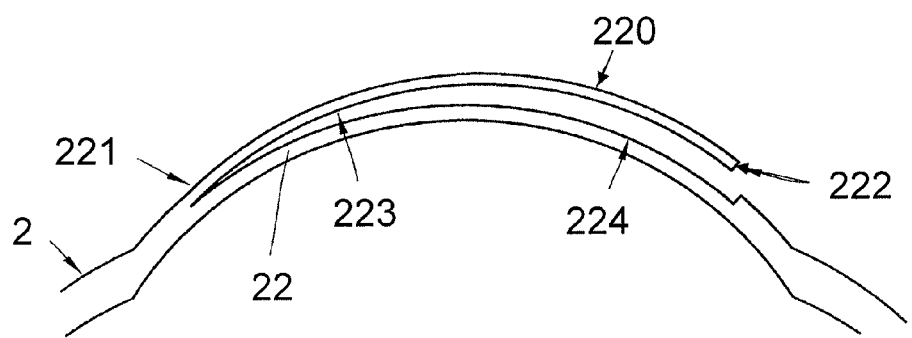
FIG. 9: schematically shows a cross section of a tissue flap ("flap") cut into the cornea, which flap remains connected to the eye in a remaining area.
Figure 10:
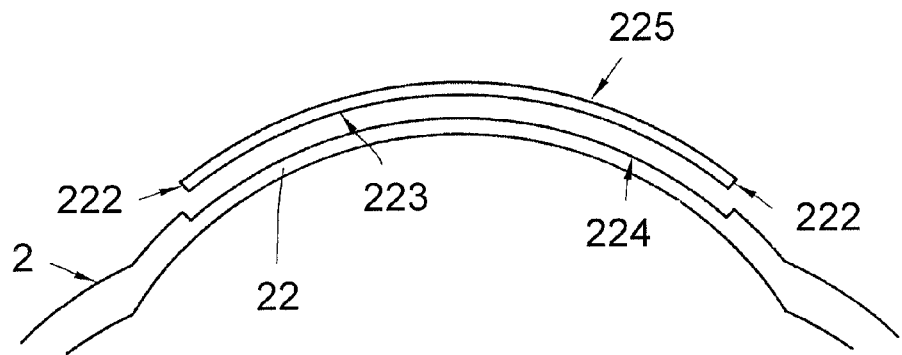
FIG. 10: schematically shows a cross section of a tissue part cut off the cornea for a partial corneal transplant.

As respectively illustrated in cross section in FIGS. 9 and 10, the second mode of operation is used, for example, for cutting tissue pieces in the cornea 22. In the example shown in FIG. 9, a tissue flap 220 ("flap") which remains connected to the eye 2 in a remaining area 221 is created, in the applanated state of the cornea 22, in the interior of the cornea 22, for example for a Lasik treatment, by means of a horizontal cut 224 extending parallel to the contact body surface (or normal to the projection direction z). The tissue flap 220 has side surfaces 222 which, in the applanated state of the cornea 22, are created by a vertical cut extending in the projection direction z. In the example shown in FIG. 10, a portion 225 of the cornea 22 is cut away from the interior of the cornea 22, e.g. for a lamellar corneal transplant, in the applanated state of the cornea 22 by means of a horizontal cut 224 extending normally to the projection direction z, with said portion being delimited circumferentially by side surfaces 222 which, in the applanated state of the cornea 22, are created by a circumferential vertical cut extending in the projection direction z.

Figures 12, 13:
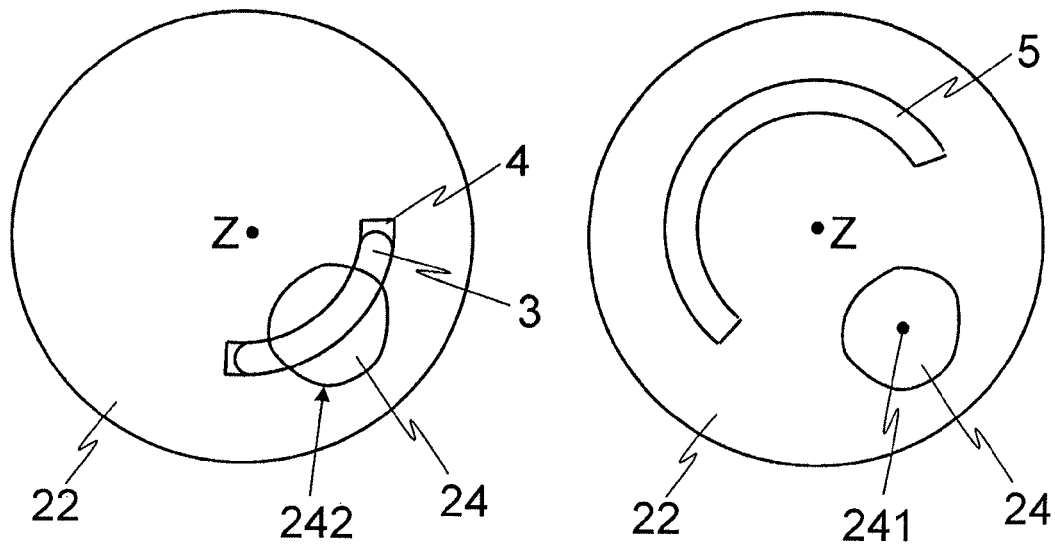
FIG. 12: schematically shows a plan view of the support of a keratoconus by means of a mechanical support insert, which has been inserted into a curved pocket cut into the cornea.
FIG. 13: schematically shows a plan view of a curved pocket, cut into the cornea, for holding an implant for pulling flat a bulging of the cornea caused by a keratoconus.

The second mode of operation is moreover used to cut pockets, lenticles by means of at least two curved intersecting surfaces, and lamellar cuts in the cornea 22. As respectively illustrated in a plan view of the cornea 22 in FIGS. 12 to 15, the second mode of operation is used for cutting pockets into the cornea 22, for example when treating a keratoconus 24, i.e. an abnormal thinning and bulging of the cornea 22 (corneal thinning). FIG. 12 illustrates supporting the keratoconus 24 by means of an implant 3 (mechanical support insert), for example, a so-called Intac made of plastic, which is introduced into a pocket 4 cut into the cornea 22. In the example shown in FIG. 12, the pocket 4 is cut arranged centered with respect to the keratoconus edge 242, with the curvature of the pocket 4 for example being defined by a circular arc around the center of the pupil Z.

FIG. 13 illustrates the pulling flat of the bulge in the cornea 22 caused by the keratoconus 24 by means of an implant (not shown), which is introduced into a pocket 5 cut into the cornea 22. In the example shown in FIG. 13, the pocket 5 is cut arranged on the side of the center of the pupil Z lying opposite to the keratoconus center 241, with the curvature of the pocket 5 for example being defined by a circular arc around the center of the pupil Z.

Figures 14, 15:
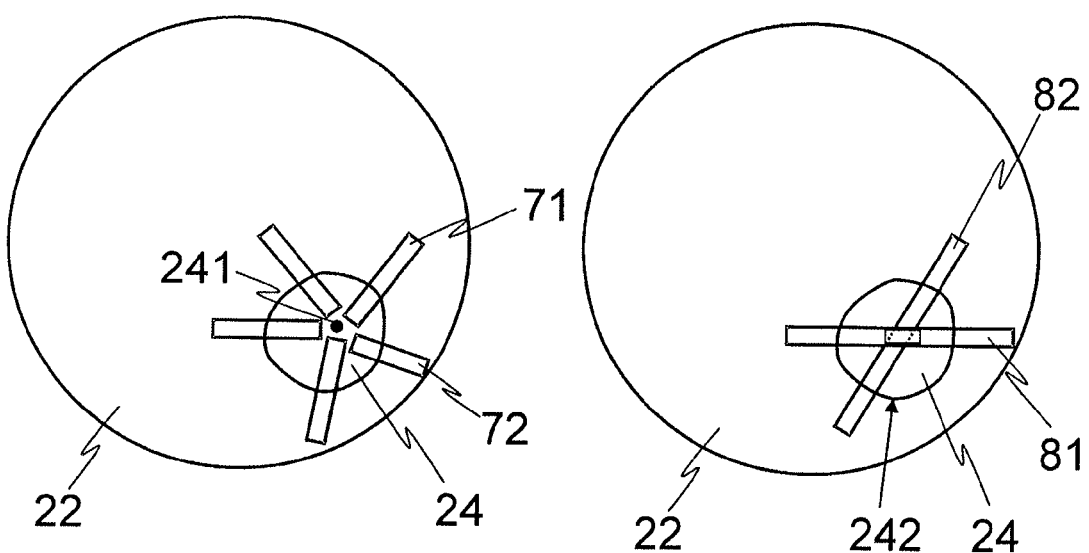
FIG. 14: schematically shows a plan view of a plurality of pockets, arranged in star formation and cut into the cornea, for correcting a keratoconus.
FIG. 15: schematically shows a plan view of two pockets, lying over one another at a distance and arranged such that they cross, cut into the cornea for inserting support inserts for supporting a keratoconus.

FIG. 14 illustrates the correction of the keratoconus 24, by cutting a plurality of pockets 71, 72 into the cornea 22. In the example shown in FIG. 14, the pockets 71, 72 are cut arranged in a star-shaped fashion with respect to the keratoconus center 241, with the punctures or openings of the pockets 71, 72 respectively being cut into the side of the pockets 71, 72 facing away from the keratoconus center 241.

FIG. 15 illustrates the support of the keratoconus 24 by means of mechanical support inserts which are introduced into pockets 81, 82 which lie over one another at a distance and are cut into the cornea 22 such that they cross. In the example shown in FIG. 15, the cross shape defined by the cut surfaces is arranged centered with respect to the keratoconus edge 242.

As an alternative to the introduction of stabilizing implants, use can also be made of adhesives. In this context, riboflavin should be mentioned in particular; it can be activated by irradiation with UVA. If the riboflavin taken up by the tissue should be activated by means of the laser beam L, the focusing system 10 can also set a wide and stretched beam waist. As a result, it is possible to expose large areas of tissue more quickly than with a sharply focused beam.

A third mode of operation is provided for disintegrating eye tissue in the sclera 23 of the eye or cloudy cornea 22 by focusing pulsed laser beams L in the IR-B infrared range by means of a third zoom function 103, e.g. onto the imaging surface F3 with a spot S3, which has a spot size with a diameter d3 (see FIG. 1).

A fourth mode of operation is provided for creating tissue cuts in the front capsular bag of the lens 21 of the eye by focusing the pulsed laser beams L in the UVA ultraviolet range by means of a fourth zoom function 104. In the fourth mode of operation, a cylindrical opening is cut into the anterior capsular bag of the lens 21 of the eye by means of, for example, a vertical circumferential cut which extends in the projection direction z, through which opening the segmented or fragmented lens 21 of the eye can be removed and be replaced by an artificial lens.

Figure 11:
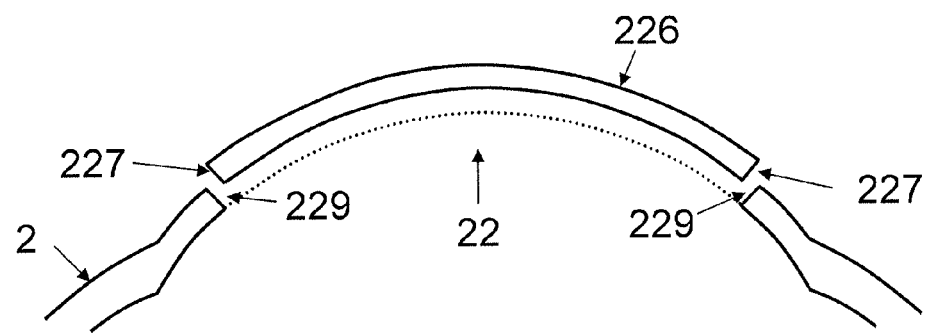
FIG. 11: schematically shows a cross section of a cornea cut off the eye for a complete corneal transplant.

A fifth mode of operation is provided for creating vertical (i.e. extending substantially normally to a reference surface applied to the cornea, for example by means of a contact body 110) tissue cuts in the cornea 22 by focusing pulsed laser beams L in the IR-A infrared range by means of a fifth zoom function 105. As illustrated in FIG. 11 in a cross section, the fifth mode of operation is used, for example, for cutting off the cornea 22 for a complete corneal transplant. In the example shown in FIG. 11, a vertical circumferential cut 229 extending in the projection direction z cuts through the cornea 22 in penetrating fashion in the applanated state of the cornea 22 and separates at least one corneal portion 226 from the eye 2. Since the cuts in this application lie outside of the optical zone of the eye 2, optically rough surfaces are not bothersome. Deformations (typically 2-20 µm) in the tissue as a result of strong gas development as a result of higher pulse energies are also uncritical. On the contrary, wider, stretched beam waists render it possible to cut faster and achieve complete tissue separation.

The invention claimed is:

1. An ophthalmological device for treating eye tissue by means of pulsed laser beams, comprising:
   a user interface configured to receive from a user a selected mode of operation,
   a laser system which is configured, in a first mode of operation, to generate a pulsed laser beam with a wavelength in the NIR (near-infrared) range and, in a second mode of operation, to generate a pulsed laser beam with a wavelength in the UVA (ultraviolet A) range, and
   a control system configured to set the wavelength of the pulsed laser beams depending on the user selected mode of operation,
   a focusing system comprising a projection optical unit, the projection optical unit including an optical system controlled by the control system, the optical system being configured for being adjusted by the control system to adjust an imaging surface and a spot size defined by the pulsed laser beam, for projection of the pulsed laser beam, the focusing system further having a drive system controlled by a plurality of zoom functions for controlling the optical system, the control system further configured to select one of the zoom functions depending on the user selected mode of operation, wherein in the first mode of operation, the control system selects a first zoom function configured to control the optical system:

to project the pulsed laser beam in the NIR range such that a narrowest beam waist of the pulsed laser beam is projected onto an imaging surface, the imaging surface being in the lens of the eye, and to refocus the pulsed laser beam in the NIR range on the imaging surface in the lens of the eye with a first spot size which has a diameter defined by the control system for the first mode of operation for disintegrating eye tissue of the lens, and in the second mode of operation, the control system selects a second zoom function which differs from the first zoom function and is configured to control the optical system:

to project the pulsed laser beam in the UVA range such that a narrowest beam waist of the pulsed laser beam is projected onto an imaging surface, the imaging surface being in the cornea of the eye, and to refocus the pulsed laser beam in the UVA range on the imaging surface in the cornea of the eye with a second spot size which is substantially smaller than the first spot size and has a diameter defined by the control system for the second mode of operation, for creating tissue cuts in the cornea.

2. The device of claim 1, wherein the focusing system comprises two optical systems which can each be set by the zoom functions to project the pulsed laser beams onto an imaging surface defined by the pulsed laser beam, and to focus said laser beams to a spot size on the imaging surface.

3. The device of claim 2, wherein the focusing system is configured, in the first mode of operation and by using the first zoom function, to set the optical systems to project the pulsed laser beams in the NIR range onto the imaging surface situated in the lens of the eye and, on the imaging surface situated in the lens of the eye, to focus said pulsed laser beams with the first spot size; and wherein the focusing system is configured, in the second mode of operation and by using the second zoom function, to set the optical systems to project the pulsed laser beams in the UVA range onto the imaging surface situated in the cornea of the eye and, on the imaging surface situated in the cornea of the eye, to focus said pulsed laser beams onto with the second spot size.

4. The device of claim 1, wherein the focusing system comprises at least one of the following: optical lenses that are inserted into the beam path, deformable mirrors, and mechanically embodied zoom curves for carrying out the zoom functions and zoom functions with digitized zoom curves for a control system.

5. The device of claim 1, wherein the laser system is configured, in the first mode of operation, to generate pulsed laser beams with a wavelength in the IR-A range and, in a third mode of operation, to generate pulsed laser beams with a wavelength in the IR-B range and wherein the focusing system is configured, in the third mode of operation, to project the pulsed laser beams in the IR-B range in focus into the sclera of the eye or into a cloudy cornea for the purpose of disintegrating eye tissue.

6. The device of claim 5, wherein the focusing system is configured, in the third mode of operation and by using a third zoom function, to project the pulsed laser beams in the IR-B range onto an imaging surface situated in the sclera of the eye or in a cloudy cornea and to focus said pulsed laser beams onto with a third spot size.

7. The device of claim 1, wherein the laser system is configured, in various modes of operation, to generate pulsed laser beams with different wavelengths and wherein the focusing system is configured, in the various modes of operation, to project the pulsed laser beams with the different wavelengths into the eye tissue being treated, respectively focused by a different zoom function associated with the relevant corresponding wavelength.

8. The device of claim 1, wherein the control system is further configured to control the device in accordance with different modes of operation, wherein the modes of operation comprise at least one of the following:

the first mode of operation is for disintegrating eye tissue of the lens of the eye by focusing pulsed laser beams in the IR-A range by the first zoom function, the second mode of operation is for creating horizontal tissue cuts in the cornea by focusing the pulsed laser beams in the UVA range by the second zoom function, a third mode of operation for disintegrating eye tissue of the sclera of the eye or the cloudy cornea by focusing pulsed laser beams in the IR-B range by a third zoom function, a fourth mode of operation for creating tissue cuts in the capsular bag of the lens of the eye by focusing the pulsed laser beams in the UVA range by a fourth zoom function, and a fifth mode of operation for creating vertical tissue cuts in the cornea by focusing pulsed laser beams in the IR-A range by a fifth zoom function.

9. The device of claim 1, wherein the projection optical unit has a numerical aperture NA<0.3.

10. The device of claim 1, wherein the projection optical unit has a numerical aperture NA<0.2.

11. The device of claim 1, wherein the projection optical unit comprises glasses having a refractive index n<1.65.

12. The device of claim 1, wherein the projection optical unit has a numerical aperture NA<0.5.

13. The device of claim 1, wherein the projection optical unit comprises glasses having a refractive index n<1.65 and being made of fused quartz.

14. The device of claim 1, wherein the projection optical unit comprises glasses made of fused quartz.

15. The device of claim 1, further comprising a scanner for deflection of said laser beam, wherein the projection optical unit is arranged downstream from said scanner.

16. An ophthalmological device for treating eye tissue by means of pulsed laser beams, comprising:

a control system configured to determine a selected mode of operation depending on a detected device type of at least one of: an application head, a projection optical unit, and a contact body connected to the ophthalmological device, a laser system which is configured, in a first mode of operation, to generate a pulsed laser beam with a wavelength in the NIR (near-infrared) range and, in a second mode of operation, to generate a pulsed laser beam with a wavelength in the UVA (ultraviolet A) range, the control system further configured to set the wavelength of the pulsed laser beams depending on the selected mode of operation, a focusing system comprising a projection optical unit, the projection optical unit including an optical system controlled by the control system, the optical system being configured for being adjusted by the control system to adjust an imaging surface and spot size defined by the pulsed laser beam, for projection of the pulsed laser beam, the focusing system further having a drive system controlled by a plurality of zoom functions for controlling the optical system, the control system further configured to select one of the zoom functions depending on the selected mode of operation, wherein in the first mode of operation, the control system selects a first zoom function configured to control the optical system:

to project the pulsed laser beam in the NIR range such that a narrowest beam waist of the pulsed laser beam is projected onto an imaging surface, the imaging surface being in the lens of the eye, and to refocus the pulsed laser beam in the NIR range on the imaging surface in the lens of the eye with a first spot size which has a diameter defined by the control system for the first mode of operation for disintegrating eye tissue of the lens, and in the second mode of operation, the control system selects a second zoom function which differs from the first zoom function and is configured to control the optical system:

to project the pulsed laser beam in the UVA range such that a narrowest beam waist of the pulsed laser beam is projected onto an imaging surface, the imaging surface being in the cornea of the eye, and to refocus the pulsed laser beam in the UVA range on the imaging surface in the cornea of the eye with a second spot size which is substantially smaller than the first spot size and has a diameter defined by the control system for the second mode of operation, for creating tissue cuts in the cornea.

17. The device of claim 16, further comprising a scanner for deflection of said laser beam, wherein the projection optical unit is arranged downstream from said scanner.

* * * * *